United States Patent

Claren et al.

Patent Number: 5,899,909
Date of Patent: May 4, 1999

[54] SURGICAL INSTRUMENT FOR TREATING FEMALE URINARY INCONTINENCE

[75] Inventors: Jan Claren, Lund; Ulf Ulmsten, Danderyd, both of Sweden

[73] Assignee: Medscand Medical AB, Malmo, Sweden

[21] Appl. No.: 08/804,680

[22] Filed: Feb. 25, 1997

[30] Foreign Application Priority Data

Aug. 30, 1994 [SE] Sweden .................................. 9402872
Oct. 9, 1995 [SE] Sweden .................................. 9503512

[51] Int. Cl.⁶ .................................................. A61B 17/42
[52] U.S. Cl. ............................ 606/119; 606/118; 606/185
[58] Field of Search ..................................... 606/118, 119, 606/138, 139, 140, 141, 148, 222, 223, 224, 225, 226, 227, 228

[56] References Cited

U.S. PATENT DOCUMENTS

| | | | |
|---|---|---|---|
| 3,182,662 | 5/1965 | Shirodkar | 606/139 |
| 4,509,516 | 4/1985 | Richmond | 128/303 R |
| 5,032,508 | 7/1991 | Naughton et al. | 435/32 |
| 5,112,344 | 5/1992 | Petros et al. | |
| 5,281,237 | 1/1994 | Gimpelson | 606/144 |
| 5,383,904 | 1/1995 | Totakura et al. | 606/228 |

FOREIGN PATENT DOCUMENTS

0598976  2/1993  European Pat. Off.
90/03766  4/1990  WIPO.

Primary Examiner—Michael Buiz
Assistant Examiner—Vy Quang Bui
Attorney, Agent, or Firm—Merchant, Gould, Smith, Edell, Welter & Schmidt, P.A.

[57] ABSTRACT

A surgical instrument and a method for treating female urinary incontinence. The instrument comprises a shank having a handle at one end thereof, and two curved needle-like elements which are connected at one end thereof each with one end of a tape intended to be implanted into the body. These elements can be connected one at a time with the shank at the other end thereof to form a curved end portion of the shank and are intended to be passed into the body via the vagina, each element being dimensioned to extend from the inside of the vaginal wall over the back of the pubic bone to the outside of the abdominal wall. When practicing the method the tape is passed into the body via the vagina first at one end and then at the other end at one side and the other, respectively, of the urethra to form a loop around the urethra, located between urethra and the vaginal wall. The tape is extended over the pubis and through the abdominal wall and is tightened. Then, the tape ends are cut at the abdominal wall, and the tape is left implanted in the body.

32 Claims, 12 Drawing Sheets

SURGICAL INSTRUMENT FOR TREATING FEMALE URINARY INCONTINENCE

FIELD OF THE INVENTION

The invention relates to a surgical instrument and a method for treating female urinary incontinence, i.e. incapacity of controlling the discharge of urine.

BACKGROUND OF THE INVENTION

Urinary incontinence may be caused by a defect function in the tissue or ligaments connecting the vaginal wall with the pelvic muscles and pubic bone.

U.S. Pat. No. 5,112,344 describes a method for treating female urinary incontinence without the necessity of opening the abdomen, which would require hospital care for may be four days. In this method a tape is looped around the muscle tissue of the abdomen to either side of urethra to be implanted into the soft tissue between the vaginal wall and the abdominal wall extending over pubis and with the ends of the tape extending into vagina. The tape is left in the body in order that fibrous tissue shall develop around the tape, said scar tissue functioning as a supporting ligament in the soft tissue. The tape is removed from the body when such scar tissue has developed, which takes about two months.

A surgical instrument of special construction is also proposed for use with this method, comprising a shank having a handle at one end thereof and a curved portion at the other end thereof said portion being intended to be passed into the body via the vagina.

The result obtained by such surgery is not always satisfactory due to the fact that fibrous tissue will not develop sufficiently since the soft tissue between the vaginal wall and the abdominal wall is in bad condition.

SUMMARY OF THE INVENTION

The object of the invention is to provide improved and simplified surgery with a considerably improved prognosis with regard to restoration of the urinary continence. For this purpose the invention provides a surgical instrument for treating female urinary incontinence of the kind referred to above, comprising a shank, a handle at one end of said shank, a tape to be permanently implanted into the body as a loop around urethra, two curved needle-like elements which are each connected at one end thereof to one end and the other of said tape, and means on said shank and each of said elements for exchangeable connection of the elements one at the time to the shank at the other end thereof to form at said other end a curved end portion dimensioned to extend from the inside surface of the vaginal wall over the back of the pubic bone to the outside of the abdominal wall.

The invention also provides a method for treating female urinary incontinence comprising the steps of passing a tape into the body via the vagina first at one end thereof and then at the other end thereof at one side and the other, respectively, of urethra to form a loop around urethra, located between urethra and the vaginal wall, extending said tape over the pubic bone and through the abdominal wall, the ends of the tape being available outside the abdominal wall, tightening said strap at said ends, and leaving the tape implanted in the body. Preferably the tape is left permanently in the body to provide itself, as an artificial ligament, the reinforcement of the tissue required in order to restore the urinary continence, and/or to provide said reinforcement by the development of fibrous tissue.

BRIEF DESCRIPTION OF THE DRAWINGS

The invention will be explained in more detail with reference to the accompanying drawings which disclose embodiments of the surgical instrument according to the invention as well as several surgical steps when practising the method of the invention using said surgical instrument In the drawings

DETAILED DESCRIPTION OF PREFERRED EMBODIMENTS

Figure 1:
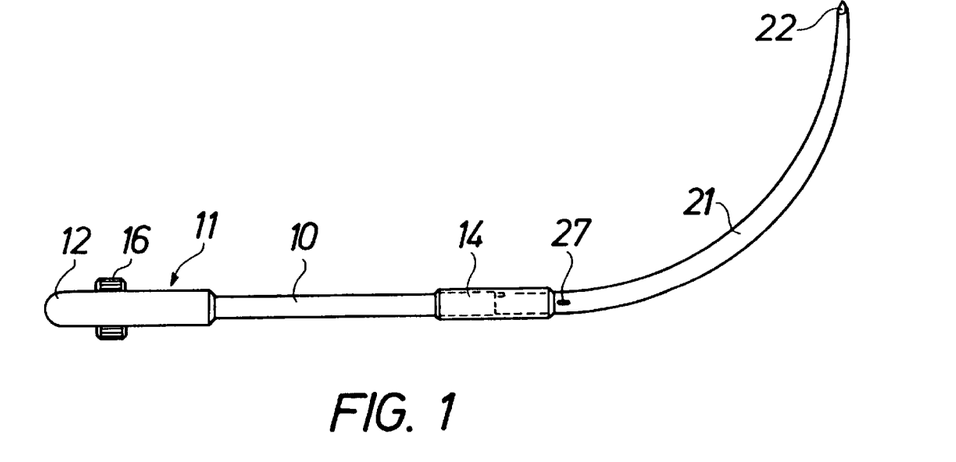
FIG. 1 is a side view of the surgical instrument in one embodiment thereof.
Figure 2:
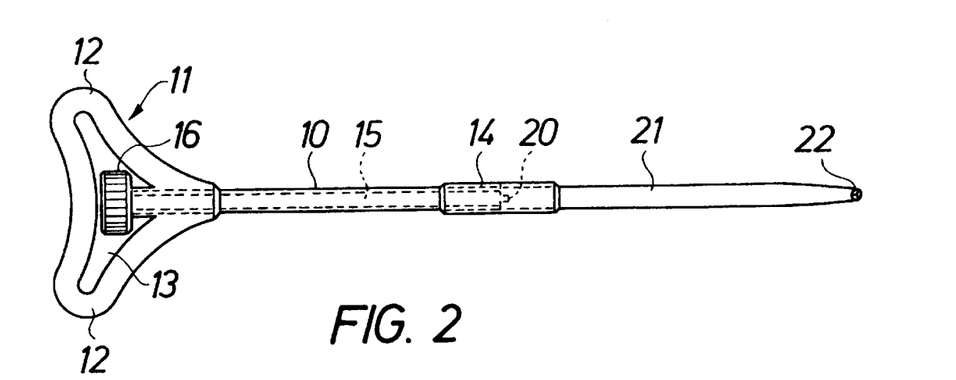
FIG. 2 is a plan view of the surgical instrument.
Figure 3:
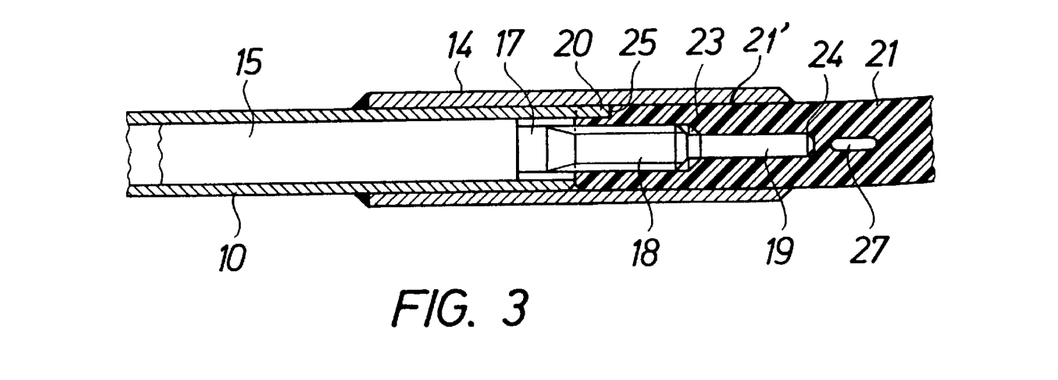
FIG. 3 is an enlarged fragmentary axial cross sectional view of a coupling of the instrument for attaching an exchangeable part thereof.

The surgical instrument of FIGS. 1 to 3 comprises a cylindrical tubulary shank 10 having at one end thereof a handle 11 which forms two in opposite directions in a common plane projecting wings 12 and an opening 13. At the other end of the shank there is a socket 14 which is partly passed onto the shank and is soldered or brazed to the shank, a portion of the socket projecting from the shank at said other end thereof. A cylindrical shaft 15 is rotatably mounted in the shank and can be rotated manually by means of a knob 16 axially knurled at the outside surface thereof, which is mounted to one end of the shaft and is received by opening 13. The other end of the shaft forms a cylindrical portion 17 of smaller outside diameter than the shaft, which joins a portion 18 having external threads, a smooth end portion 19 of further reduced diameter joining the threaded portion 18, end portion 19 forming a guide pin at said other end of the shaft. Portions 18 and 19 are received in the portion of socket 14 projecting from the shank, and also a shoulder 20 projecting from the shank is received in said portion.

The surgical instrument as described so far is intended to be used several times and therefore should consist of a material which can be sterilized by autoclaving, e.g. of stainless steel.

The surgical instrument also includes an exchangeable and disposable element 21 which will be termed needle. It is attached to the shank at a straight portion 21' at one end of the needle and extends over substantially a quarter of a circle to the other, free end thereof in order to follow substantially the profile of the pubis between the vagina and the abdominal wall. The needle has circular cross section and has a smooth, preferably polished outside surface. It tapers slightly towards the free end thereof where the needle forms a point 22 by being conical or, as shown, faceted but it can also be blunt-ended and have a transversely cut end. The practical use of the surgical instrument so far has shown that the conical shape of the point is preferred. The disposable needle shall be made either of a tissue compatible plastics, such as polycarbonate, or of steel or a similar material.

For attachment of needle 21 to shank 10 the needle has at said one end thereof where the needle forms said straight portion 21' to be received in socket 14, an axial blind hole extending from the end surface, said hole having a threaded portion 23 and inwardly thereof a narrower, cylindrical portion 24. Guide pin 19 is dimensioned to be guidingly received by said latter portion when the threaded portion 18 for attaching needle 21 to the rest of the surgical instrument is screwed into threaded portion 23 of the blind hole by rotating shaft 15 by manual rotation of knob 16, the end surfaces of the shank and the needle being pressed against each other. The needle should be oriented in a predetermined rotational position in relation to the shank; it should project at right angles to the plane of handle 11, and this rotational position is secured by shoulder 20 on the shank being received in a mating recess 25 in the outside surface of the needle.

Portion 23 of needle 21 instead of being threaded can be dimensioned such that the threaded portion 18 of shaft 15 cuts a thread in the material of the needle when being screwed thereinto.

When the two parts of the surgical instrument are screwed together in the manner described they form a rigid unit which can be controlled with great precision at handle 11 when it is used for surgery by applying the method of the invention.

Figure 4:
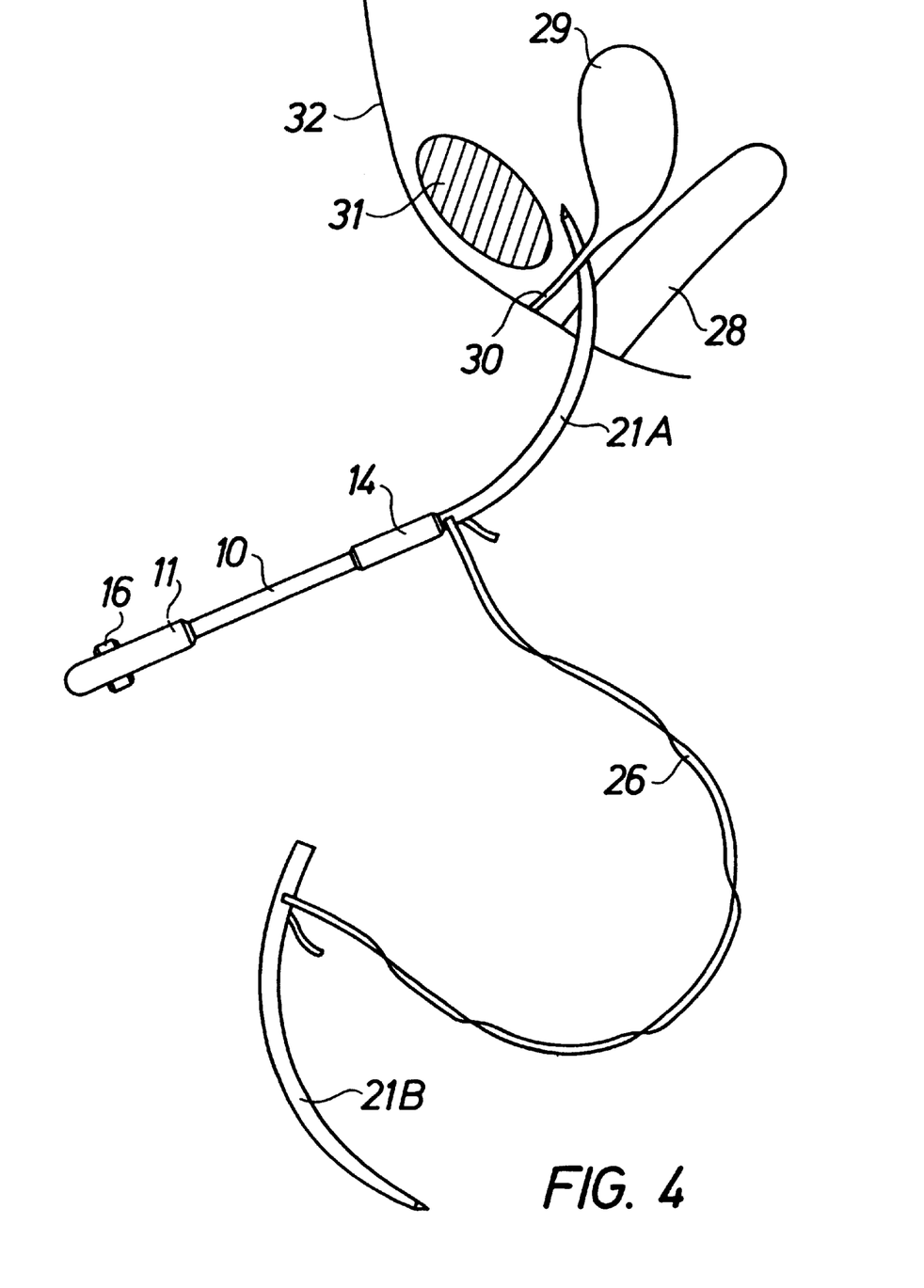
FIGS. 4 to 10 illustrate diagrammatically several surgical steps of the method according to the invention, FIG. 11 in the same way illustrates the final step of the method.

When the method according to the invention is practised two needles 21A and 21B of the embodiment described shall be connected one at each end of a tape 26, FIG. 4. The tape end can be glued to the needle but the connection can be effected also by the tape being passed through an eye 27, FIG. 3, in the needle adjacent the end attached to the shank or by the tape end being connected by ultrasonic welding to the needle or being baked into the plastics material of the needle at injection molding thereof.

When the surgery for implanting the tape shall start, one needle 21A is attached to shank 10, the other needle 21B hanging loosely in tape 26 as shown in FIG. 4.

In FIGS. 4 to 11 the relevant parts of the female lower abdomen is disclosed diagrammatically, the vagina being designated 28, the urinary bladder 29, the urethra 30, the pubic bone 31, and the abdominal wall 32.

Figure 5:
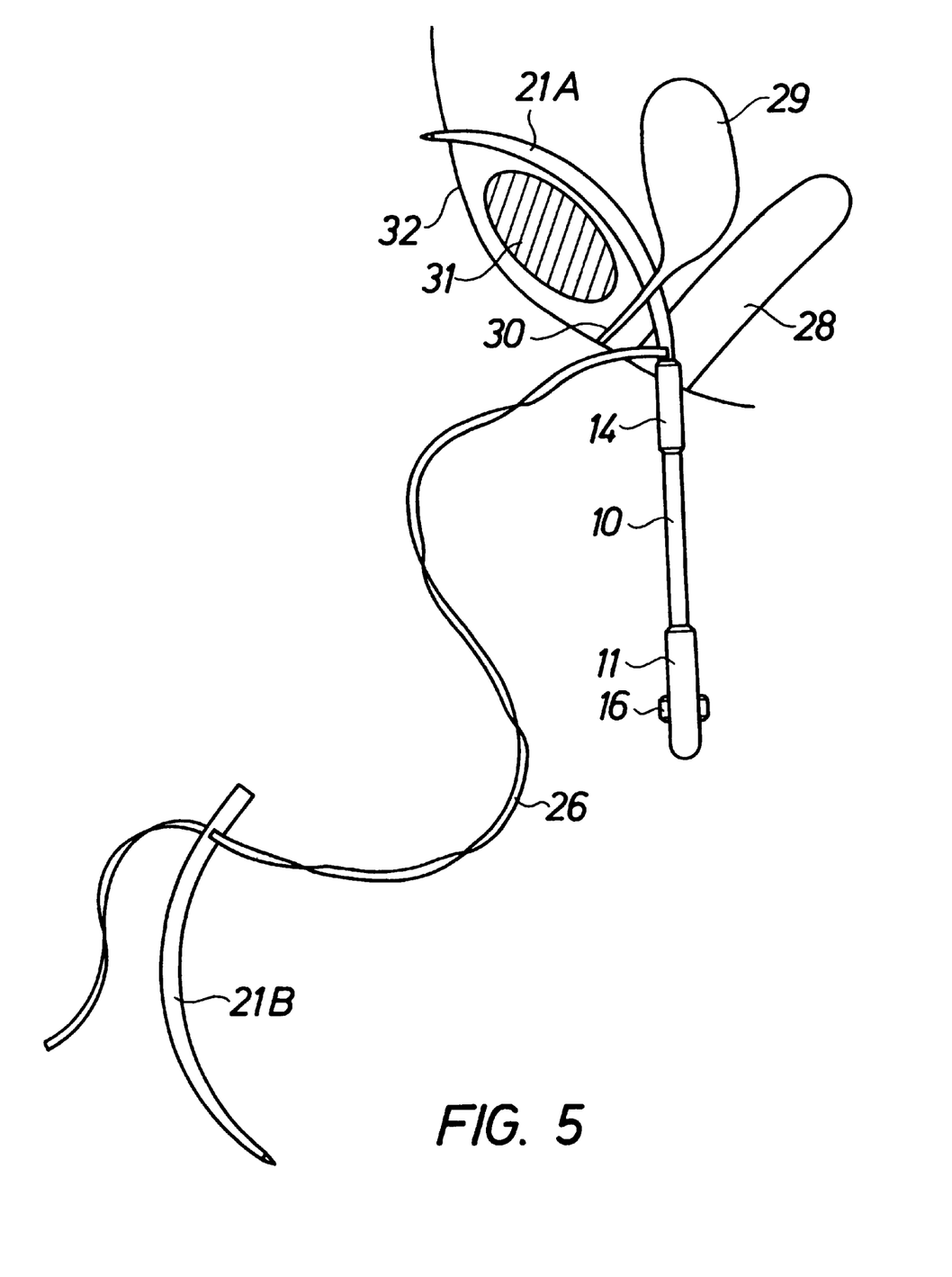

The first step of the surgery for implanting tape 26 is disclosed in FIG. 4 and comprises penetration of the vaginal wall by needle 21A, an incision having first been made in said wall, and also penetration of the soft tissue at one side of urethra 30, the needle then according to FIG. 5 being passed close to the back of the pubic bone 31 and then through the abdominal wall above the pubic bone. An incision can be done through the abdominal wall for the passage of the needle therethrough but if the needle is pointed it may be sufficient to let the needle penetrate into the abdominal wall from the inside thereof and to make a registering incision in the abdominal wall on the outside thereof.

Figure 6:
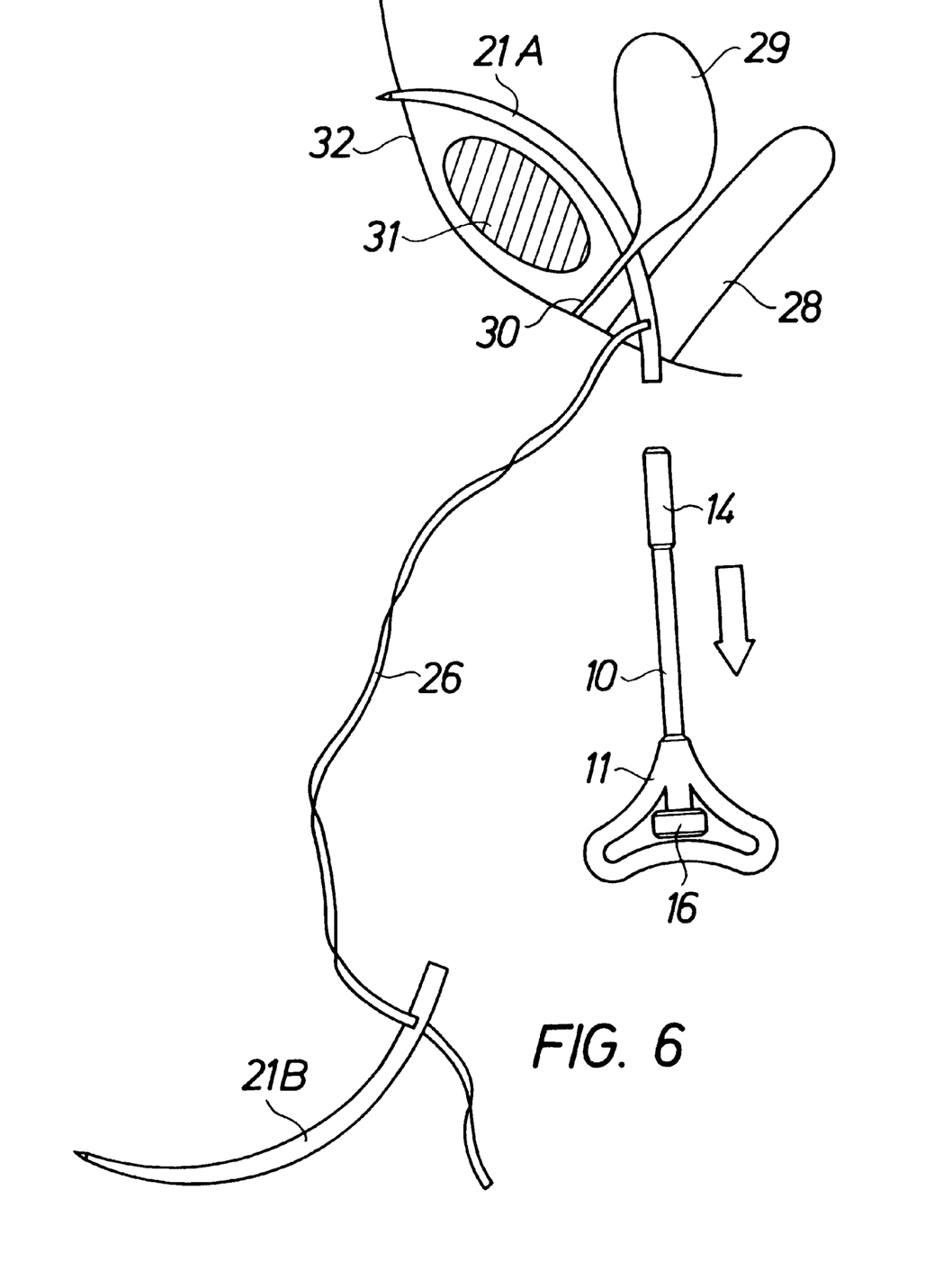
Figure 7:
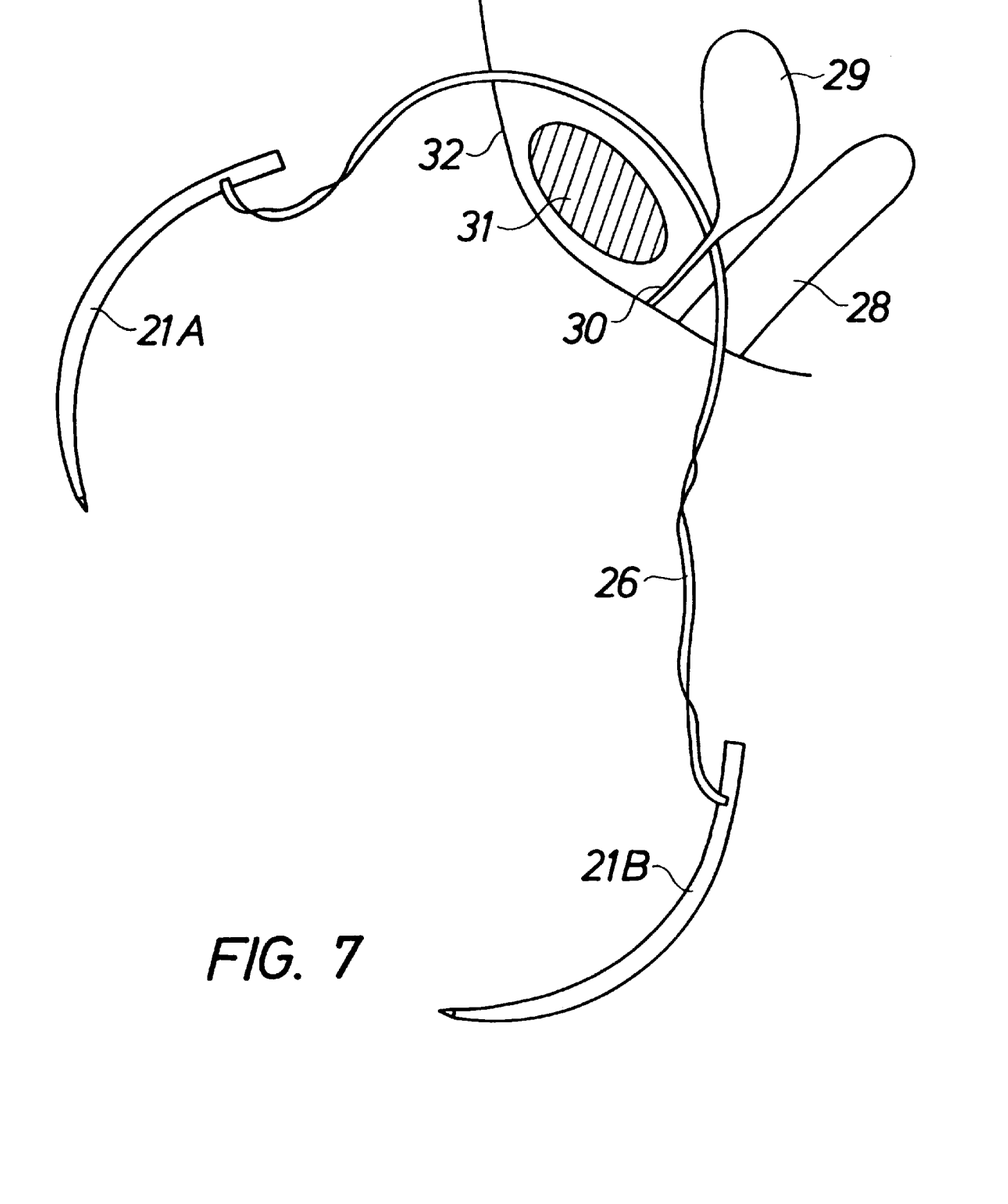

The shank of the instrument is now disconnected from needle 21A, FIG. 6, by rotating shaft 15 at knob 16 so that the threaded portion 18 of the shaft is unscrewed from the threaded portion 23 in needle 21A, said needle then being withdrawn from the abdominal wall by means of forceps and tape 26 being pulled into and through the tissue as illustrated in FIG. 7.

Figure 8:
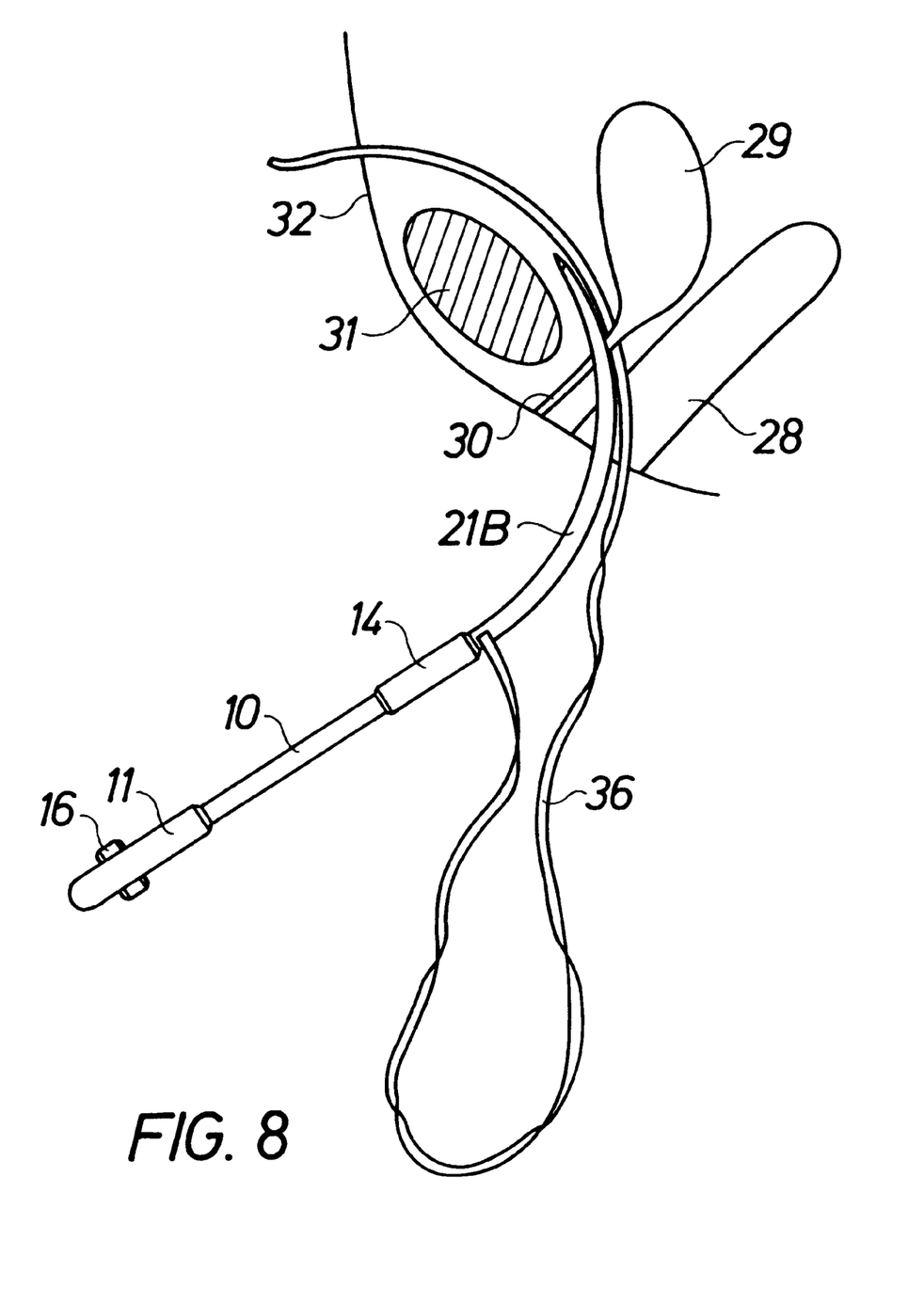
Figure 9:
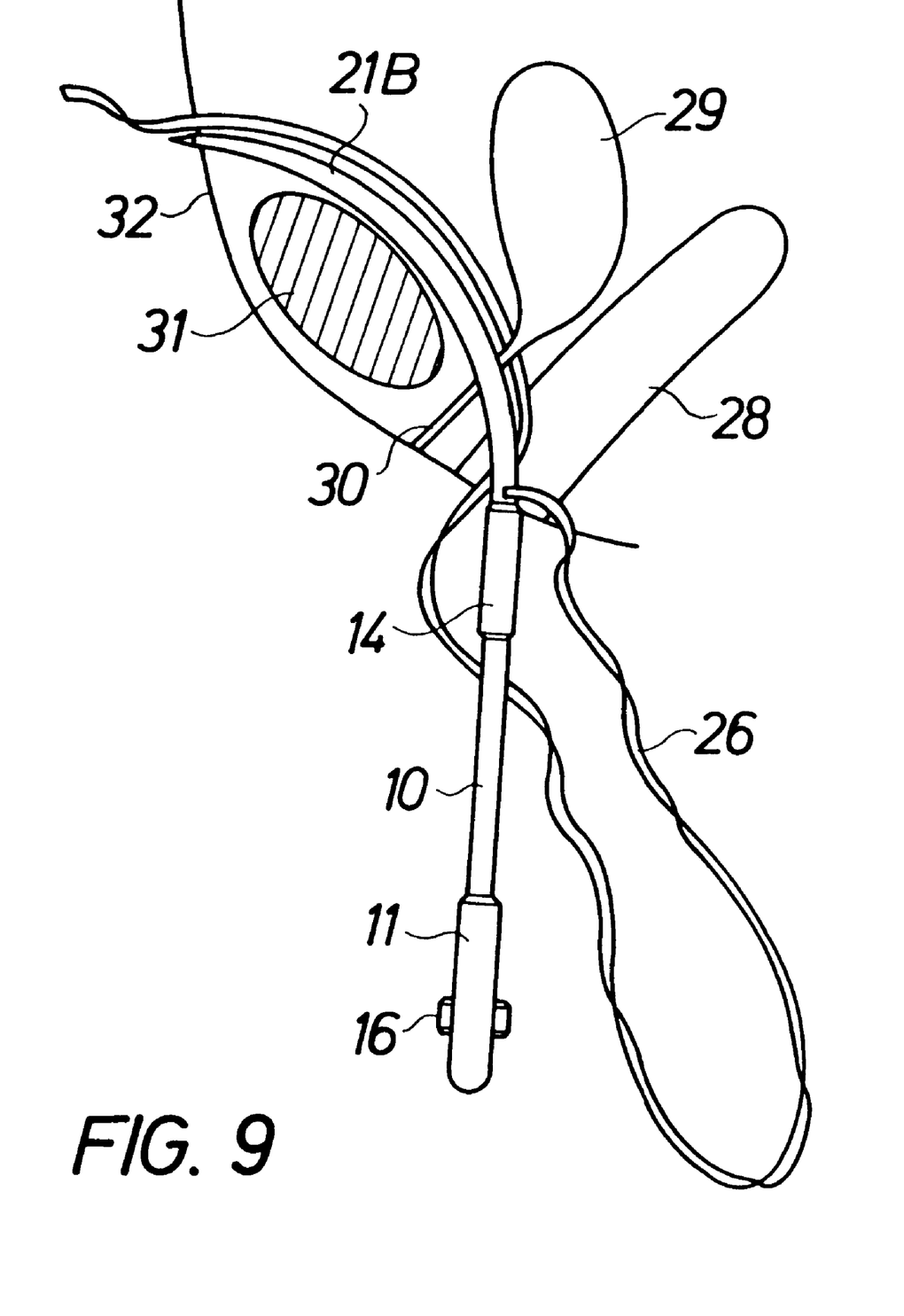

The other needle 21B is now attached to the shank, FIG. 8, and is passed through the incision in the vaginal wall to pass through the soft tissue at the other side of urethra 30. Needle 21B is passed through the abdominal wall, FIG. 9, and then, after having been disconnected from the shank, is withdrawn from the abdominal wall, FIG. 10, all in the same way as in the earlier procedure with needle 21A.

Figure 10:
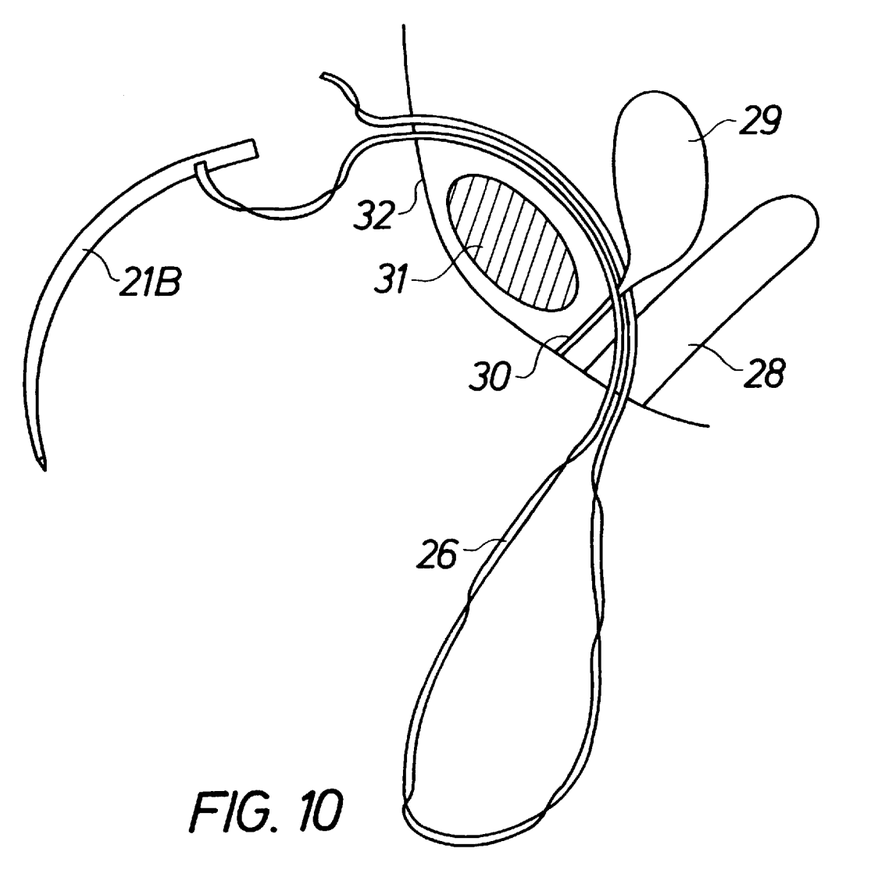
Figure 11:
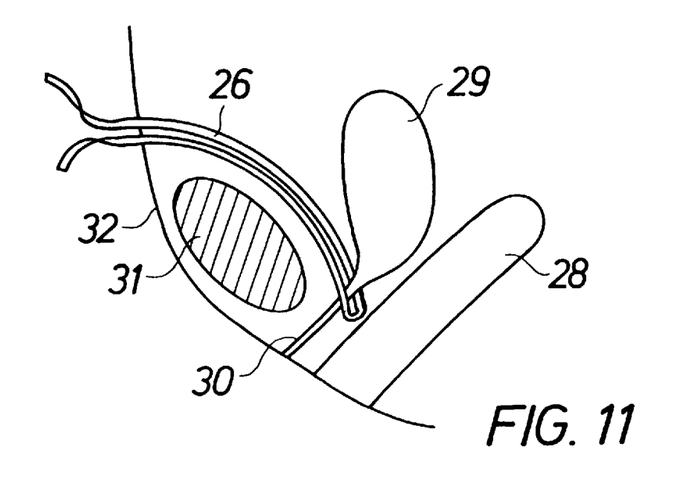
Figure 12:
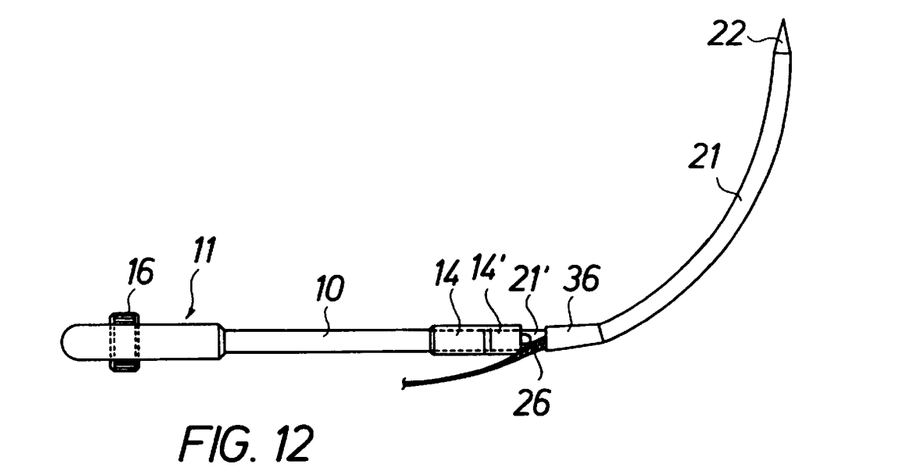
FIG. 12 is a side view of the surgical instrument in a second, preferred embodiment thereof.
Figure 13:
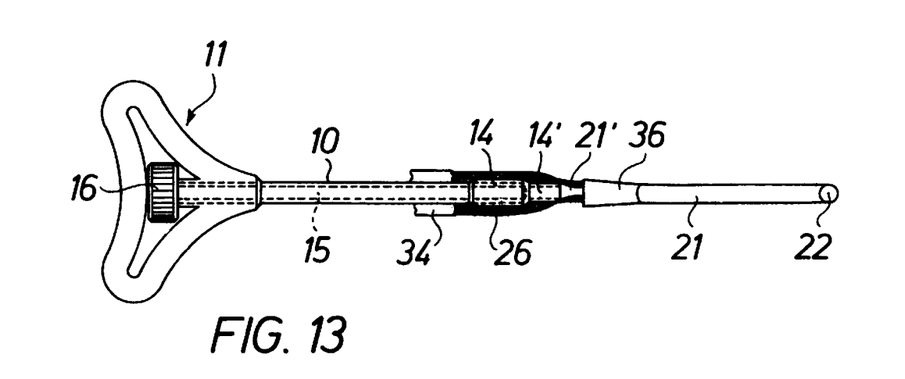
FIG. 13 is a plan view of the surgical instrument disclosed in FIG. 12.

Tape 26 is now located at each side of urethra 30 as shown in FIG. 10 and is tightened with the tape forming a loop around urethra and located between urethra and the vaginal wall, FIG. 11. The surplus of the tape at the outside of the abdominal wall is cut off. Then, the tape is left as an implant in the body to form an artificial ligament and providing the support for urethra as required in order to restore the urinary continence.

In the embodiment of FIGS. 12 to 17 the end portion 14' of socket 14 is flattened from opposite sides so that the cross section of said end portion is non-circular, and the straight portion 21' of needle 21 at the end to be attached to shank 10 is cylindrical but has milled flat faces 21" over that part of said portion 21', extending from the adjacent end of the needle, which shall be received by socket portion 14'. The predetermined rotational position of the needle in relation to the shank at right angles to the plane of handle 11 is secured by the non-circular shape of socket portion 14' and the end portion of the needle having the flat faces 21", which fits into socket portion 14'. The end portion of the needle having the flat faces 21" joins the body of the needle over a conical portion 33, which tapers towards a shoulder 33'.

In the preferred embodiment the tape comprises a mesh or netting forming openings of the order of 1 mm. in order that fibroblasts shall be able to grow into the tape for anchoring of the tape in surrounding tissue. A suitable material for the tape is PROLENE®, a knitted polypropylene mesh having a thickness of 0.7 mm manufactured by Ethicon, Inc., Sommerville, N.J., USA. This material is approved by FDA in USA for implantation into the human body.

Another kind of tape which may be used in the method according to the invention can be knitted or woven more closely than the tape mentioned above and can be of such material that the tape after a shorter or longer period will be completely resorbed. By the development of fibroblast proliferation stimulated by the tape the reinforcement of the tissue required in order to restore the urinary continence will be obtained.

The material of the tape can be coated with a fibroblast stimulating substance, e.g. an enamel matrix derivative.

Figure 14:
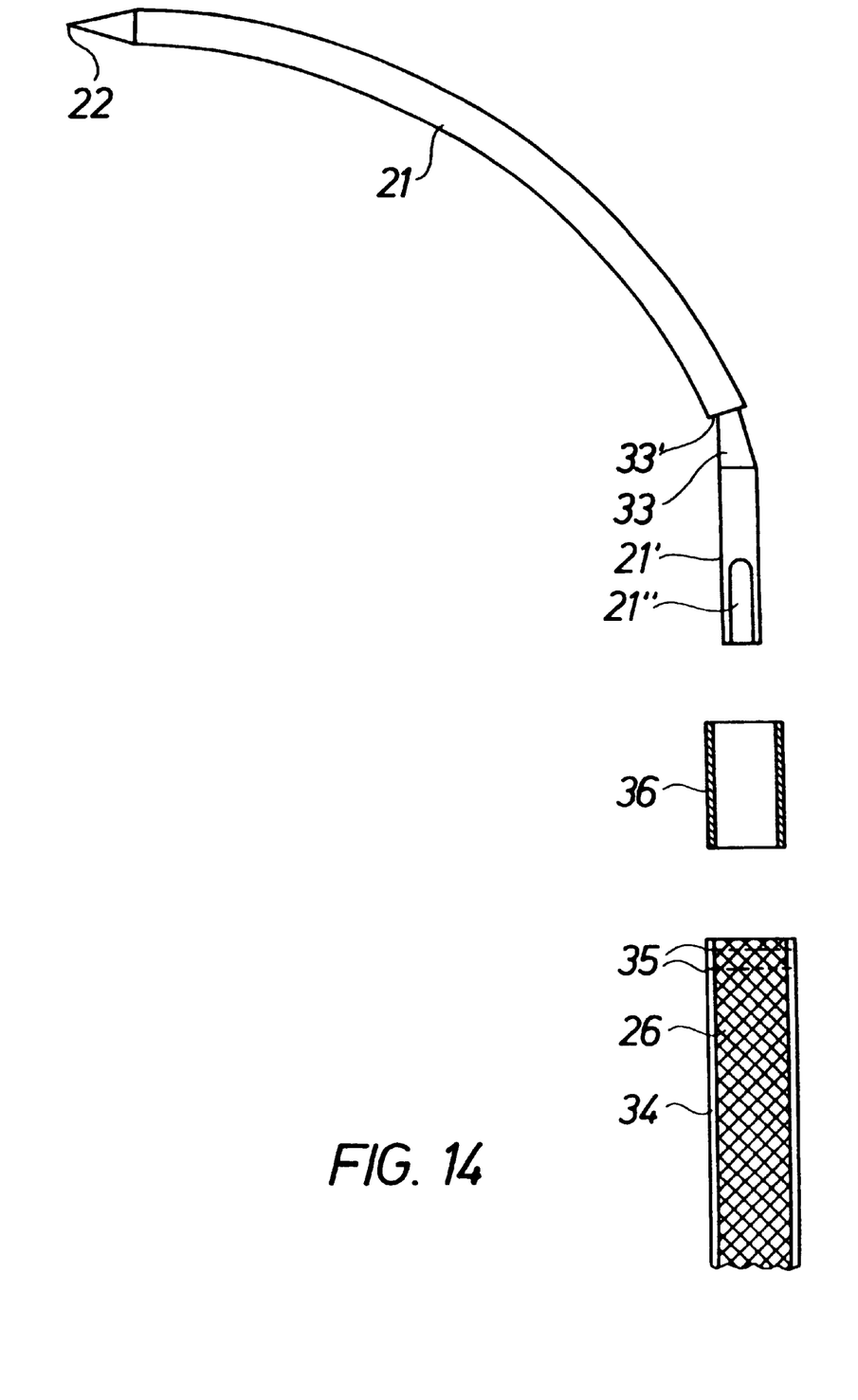
FIG. 14 is an exploded side view of one of the needles and tape and shrinkage hose to be connected with said needle.
Figure 15:
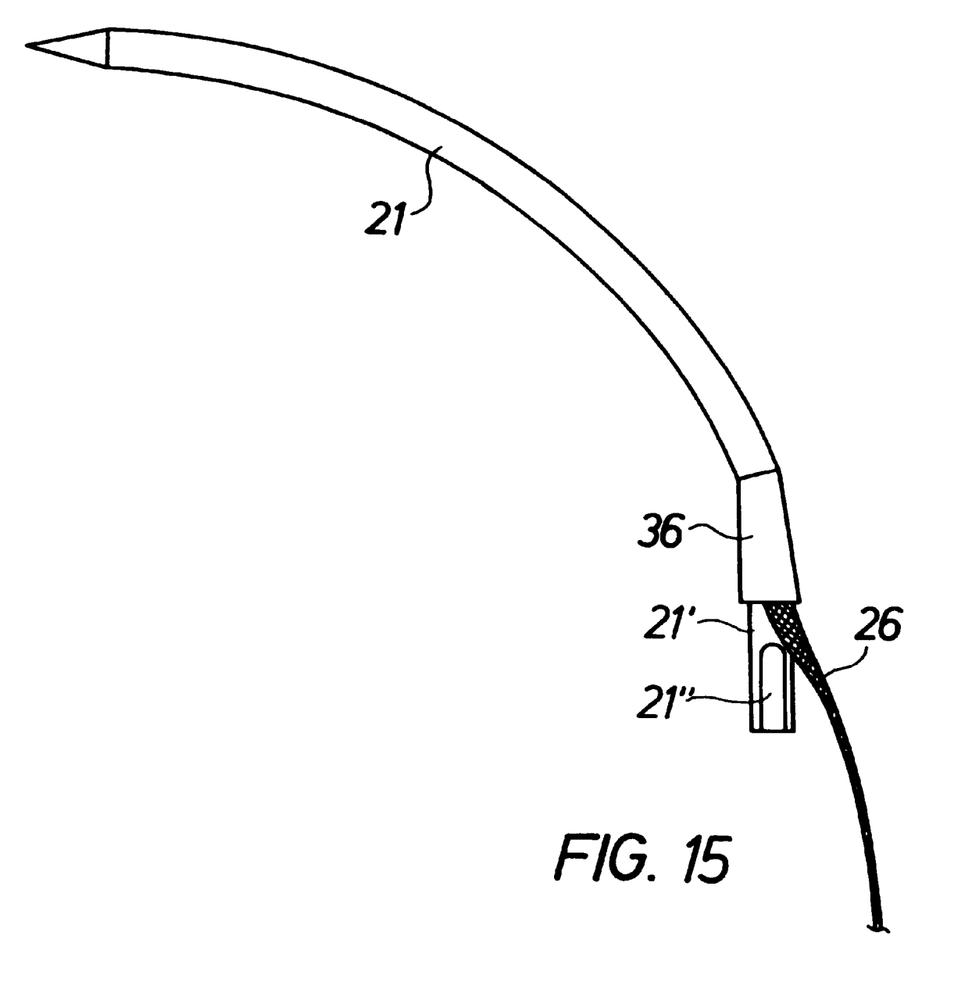
FIG. 15 is a side view of the needle in FIG. 14 with the tape connected therewith.
Figure 16:
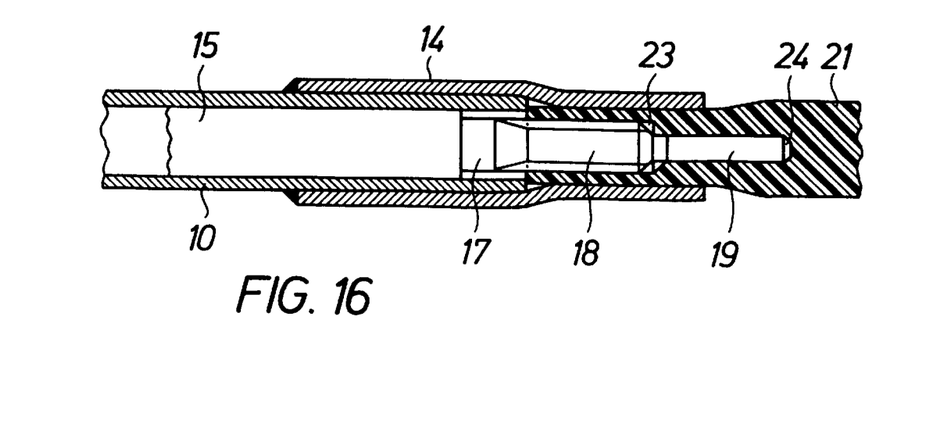
FIG. 16 is an enlarged fragmentary axial cross sectional view of a modified coupling of the instrument for connecting exchangeable needles of the kind shown in FIGS. 14 and 15.

The netting (tape) preferably has a width of approximately 10 mm and is enclosed in a thin polyethylene sheath 34 which in flattened condition has substantially the same width as the tape although a difference in width is shown in FIG. 14 in order to make the provision of the sheath more clear. The length of the netting should be approximately 400 mm. The netting and the sheath may be interconnected by means of two rows 35 of stitching as shown although this is not necessary. The end portion of the sheath is attached to the conical portion 33 of the needle by means of a shrink hose 36 of rubber which extends from the shoulder 33' over the conical portion 33 and partly over the cylindrical end portion 21' of the needle. The shrink hose is substantially flush with the surface of the needle at the shoulder. By this arrangement the netting is securely attached to the needle but if desired the connection can be supplemented by gluing the sheath to portion 33.

The purpose of sheath 34 is above all to facilitate the insertion of the netting in the manner described above i e when the netting is pulled at the ends thereof from the vaginal wall to the abdominal skin and to avoid that rough edges of the netting irritate or damage the body tissues.

Figure 17:
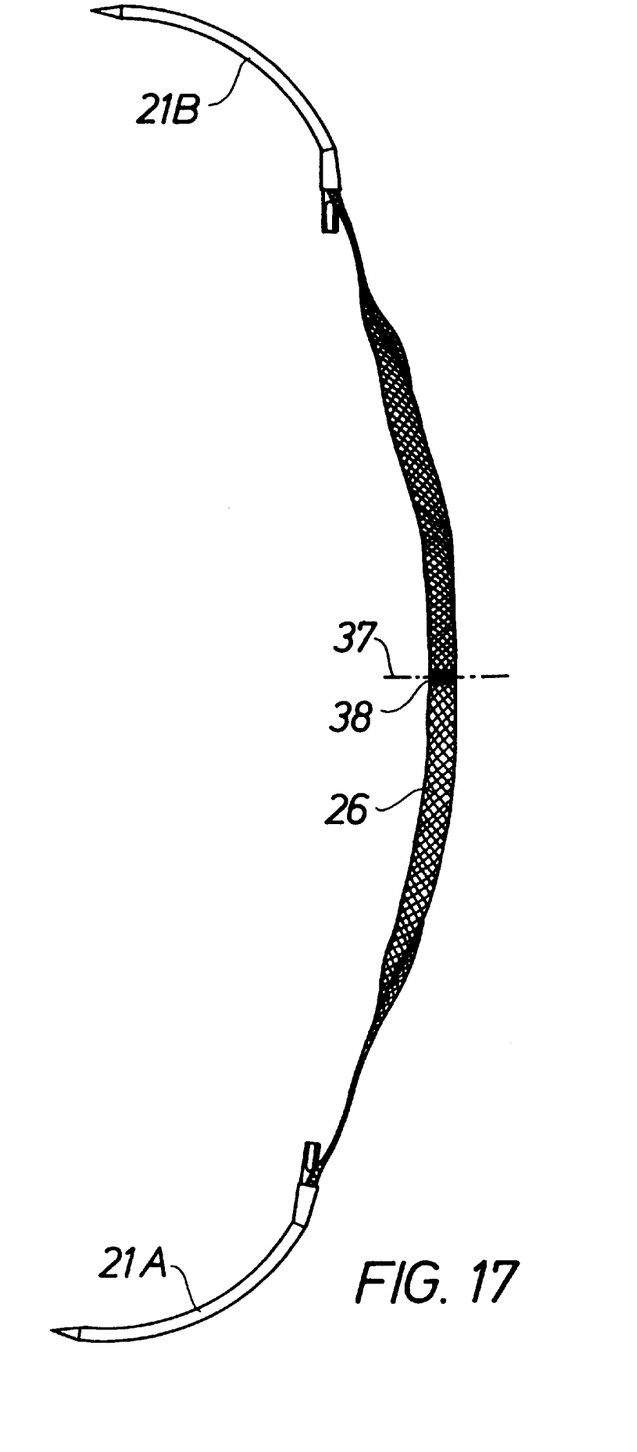
FIG. 17 is a side view of two needles and a tape interconnecting said needles.

When the tape has been positioned in the correct position as a sling around the urethra the polyethylene sheath shall be removed, and in order to facilitate the removal the sheath can be perforated at the longitudinal center thereof as indicated by a dot-and-dash line 37 in FIG. 17, so that the two halves of the sheath can be withdrawn from the body by pulling at the respective outer ends thereof the halves being separated at the perforation under the influence of the pulling force. As an alternative the sheath can be made in two halves which overlap each other without being interconnected at the longitudinal center of the netting.

The purpose of the polyethylene sheath is also to protect the netting during attachment to the needles and during handling before and during insertion into the body.

The longitudinal center of the tape and sheath should be indicated by a visible colour mark 38, FIG. 17 so that the surgeon readily can see when the netting is symmetrically located with reference to urethra during the surgery.

We claim:

1. Surgical instrument for treating female urinary incontinence, comprising a shank, a handle at one end of said shank, a tape to be permanently implanted into the body as a loop around urethra, two curved needle-like elements which are each connected at one end thereof to one end and the other of said tape, and means on said shank and each of said elements for exchangeable connection of the elements one at a time to the shank at the other end thereof to form at said other end an extension of the shank as a curved end portion thereof dimensioned to extend from the inside surface of the vaginal wall over the back of the pubic bone to the outside of the abdominal wall.

2. Instrument as in claim 1 wherein said means comprises screw coupling means.

3. Instrument as in claim 2 wherein said screw coupling means comprises a shaft rotatably mounted in said shank, an operating knob at one end of the shaft said knob being available at said one end of the shank, threads on the shaft at the other end thereof and on each of said elements for screw interengagement between the shaft and the element to be connected to the shank.

4. Instrument as in claim 1 further comprising a sleeve portion on said shank at said other end thereof to receive therein an end portion of the needle-like element to be connected to the shank.

5. Instrument as in claim 1 wherein the handle comprises two wings projecting diametrically from the shank.

6. Instrument as in claim 5 further comprising mutually cooperating means on said shank and said needle-like elements for positioning the element to be connected to the shank at right angles to the plane of the wings.

7. Instrument as in claim 1 wherein said shank is intended for use several times and consists of a material that can be autoclaved, and wherein said needle-like elements are intended for a single use.

8. Instrument as in claim 1 wherein said tape is attached to said elements by the tape ends being glued to the elements.

9. Instrument as in claim 1 wherein said tape is attached to said elements by the tape ends being welded to the elements.

10. Instrument as in claim 1 wherein said elements are made of plastics material and wherein said tape is attached to said elements by the tape ends being baked into the plastics material of the elements.

11. Instrument as in claim 1 wherein said tape is attached to said elements by the tape ends being mechanically clamped on said elements.

12. Instrument as in claim 1 wherein each of said needle-like elements forms an eye said tape at each end thereof being passed through said eye in one and the other of said elements, respectively.

13. Instrument as in claim 1 wherein said needle-like elements are curved over substantially a quarter of a circle.

14. Instrument as in claim 1 wherein each of said needle-like elements tapers towards the other, free end thereof.

15. Instrument as in claim 14 wherein each of said needle-like elements is pointed at said other end thereof.

16. Instrument as in claim 14 wherein each of said needle-like elements is blunt at said other end thereof.

17. Instrument as in claim 1 wherein said tape is perforated for growth of fibroblasts thereinto.

18. Instrument as in claim 17 wherein said tape is coated with a fibroblast stimulating material.

19. Instrument as in claim 18 wherein said tape is made of polypropylene.

20. Instrument as in claim 17 wherein said tape comprises a netting.

21. Instrument as in claim 20, further comprising a thin plastic sheath enclosing said tape.

22. Instrument as in claim 21 wherein said sheath is made of polyethylene.

23. Instrument as in claim 21 wherein said sheath has a perforation line at the longitudinal center thereof.

24. Instrument as in claim 21 wherein said sheath comprises two halves having adjacent ends overlapping each other.

25. Instrument as in claim 21 wherein each of said needle-like elements comprises a non-circular end portion fitting into a non-circular socket at said other end of the shank.

26. Instrument as in claim 25 wherein said non-circular end portion of the needle-like element joins the rest of the element by a conical portion tapering towards a shoulder on the needle-like element.

27. Instrument as in claim 26 wherein the netting and the sheath are connected to the needle-like element at said conical portion.

28. Instrument as in claim 27 further comprising a shrink hose covering said netting and said sheath at the site of attachement thereof.

29. Instrument as in claim 28 wherein one end of the shrink hose abuts said shoulder and is substantially flush with the surface of the needle-like element at said shoulder.

30. Instrument as in claim 29 wherein the netting and the sheath project from the shrink hose at the other end thereof.

31. Instrument as in claim 21 wherein a visible marking is provided on the sheath at the longitudinal center thereof.

32. Method for treating female urinary incontinence comprising the steps of passing a tape into the body via the vagina first at one end thereof and then at the other end thereof at one side and the other, respectively, of urethra to form a loop around urethra, located between urethra and the vaginal wall, extending said tape over the pubic bone and through the abdominal wall, the ends of the tape being available outside the abdominal wall, tightening said strap at said ends, and leaving the tape implanted in the body.

* * * * *

UNITED STATES PATENT AND TRADEMARK OFFICE
CERTIFICATE OF CORRECTION

PATENT NO.      : 5,899,909
DATED           : May 4, 1999
INVENTOR(S)     : Jan Claren and Ulf Ulmsten Page 1 of 1

It is certified that error appears in the above-identified patent and that said Letters Patent is hereby corrected as shown below:

Column 1,
Line 3, after the title and before the FIELD OF THE INVENTION, insert:
-- CROSS-REFERENCE TO RELATED APPLICATIONS This application is the national stage filing of internationl application number PCT/SE96/01269 filed on October 8, 1996, which claims foreign priority benefits under Title 35 US Code § 119 of Sweden application number 9503512-7 filed on October 9, 1995; and international application number PCT/SE95/00964 filed on August 28, 1995, which claims foreign priority benefits under Title 35 Code § 119 Sweden application number 9402872-7 filed on August 30, 1994. --

Signed and Sealed this

Fifth Day of July, 2005

JON W. DUDAS
*Director of the United States Patent and Trademark Office*